(12) United States Patent
Georgeson et al.

(10) Patent No.: US 10,309,893 B2
(45) Date of Patent: *Jun. 4, 2019

(54) COMPOSITE INSPECTION

(71) Applicant: The Boeing Company, Chicago, IL (US)

(72) Inventors: Gary Ernest Georgeson, Tacoma, WA (US); William P. Motzer, Charleston, SC (US); Jill Paisley Bingham, Seattle, WA (US); Alan F. Stewart, Seattle, WA (US); Steven Kenneth Brady, Renton, WA (US); James C. Kennedy, Summerville, SC (US)

(73) Assignee: The Boeing Company, Chicago, IL (US)

( * ) Notice: Subject to any disclaimer, the term of this patent is extended or adjusted under 35 U.S.C. 154(b) by 272 days.

This patent is subject to a terminal disclaimer.

(21) Appl. No.: 15/070,357

(22) Filed: Mar. 15, 2016

(65) Prior Publication Data

US 2017/0176321 A1 Jun. 22, 2017

Related U.S. Application Data

(60) Provisional application No. 62/270,546, filed on Dec. 21, 2015.

(51) Int. Cl.
  *G01N 21/17* (2006.01)
  *G01N 29/04* (2006.01)
  (Continued)

(52) U.S. Cl.
  CPC ....... *G01N 21/1702* (2013.01); *G01N 29/043* (2013.01); *G01N 29/0645* (2013.01);
  (Continued)

(58) Field of Classification Search
  CPC ............. G01N 21/1702; G01N 29/043; G01N 29/0645; G01N 29/2418; G01N 29/343;
  (Continued)

(56) References Cited

U.S. PATENT DOCUMENTS 5,010,885 A    4/1991  Fink et al.
6,298,725 B1 * 10/2001  Forrester ................ G01H 1/003
                                                 73/593
(Continued)

FOREIGN PATENT DOCUMENTS

JP    2011058937 A    3/2011

OTHER PUBLICATIONS

Understanding FFTs and Windowing, National Instrumentstm (http://download.ni.com/evaluation/pxi/Understanding%20FFTs%20and%20Windowing.pdf).*

(Continued)

*Primary Examiner* — Lisa M Caputo
*Assistant Examiner* — Suman K Nath
(74) *Attorney, Agent, or Firm* — Yee & Associates, P.C.

(57) ABSTRACT

A method of detecting inconsistencies in a composite structure is presented. A pulsed laser beam is directed towards the composite structure comprised of a number of composite materials. Wide-band ultrasonic signals are formed in the composite structure when radiation of the pulsed laser beam is absorbed by a surface of the composite structure. The wide-band ultrasonic signals are detected over a duration of time to form data. The data comprises an ultrasonic A-scan spectrum. The data is processed to identify a structure signal in a frequency domain of the ultrasonic A-scan spectrum. The structure signal of the ultrasonic A-scan spectrum is compared to a structure signal of a composite structure standard to determine whether the inconsistencies are present in the number of composite materials.

11 Claims, 12 Drawing Sheets

(51) Int. Cl.
*G01N 29/06* (2006.01)
*G01N 29/24* (2006.01)
*G01N 29/34* (2006.01)
*G01N 29/44* (2006.01)
*G01N 29/46* (2006.01)

(52) U.S. Cl.
CPC ....... *G01N 29/2418* (2013.01); *G01N 29/343* (2013.01); *G01N 29/348* (2013.01); *G01N 29/4436* (2013.01); *G01N 29/4454* (2013.01); *G01N 29/46* (2013.01); *G01N 2021/1706* (2013.01); *G01N 2291/0231* (2013.01)

(58) Field of Classification Search
CPC ............. G01N 29/348; G01N 29/4436; G01N 29/4454; G01N 29/46; G01N 2021/1706; G01N 2291/0231
USPC ......... 73/643, 610, 611, 583, 600, 602, 609, 73/615, 621
See application file for complete search history.

(56) References Cited

U.S. PATENT DOCUMENTS

| | | |
|---|---|---|
| 9,164,066 B1 | 10/2015 | Bossi et al. |
| 9,188,566 B2 | 11/2015 | Georgeson et al. |
| 9,250,213 B1 | 2/2016 | Bossi et al. |
| 2006/0235621 A1* | 10/2006 | Cole ................. G01N 21/4795 702/19 |
| 2013/0088724 A1 | 4/2013 | Dubois et al. |
| 2014/0116146 A1 | 5/2014 | Bossi et al. |
| 2016/0113507 A1* | 4/2016 | Reza ................. G01N 21/1717 356/477 |

OTHER PUBLICATIONS

Discrete Fourier transform (https://en.wikipedia.org/wiki/Discrete_Fourier_transform).*
Extended European Search Report, dated Feb. 3, 2017, regarding Application No. 16192875.9, 7 pages.
Bossi et al., "Ultrasound Inspection System for Inspecting a Test Object with Non-Planar Features," U.S. Appl. No. 13/526,853, filed Jun. 19, 2012, 62 pages.
Pelivanov et al., "A kHz rate pump-probe scanner for advanced evaluation of aircraft composites," International Symposium on Laser Ultrasonics and Advanced Sensing, paper No. 12, Jun. 2015, 3 pages.
Pelivanov et al., "A new fiber-optic non-contact compact laser-ultrasound scanner for fast non-destructive testing and evaluation of aircraft composites," Journal of Applied Physics, vol. 115, Mar. 2014, 12 pages.
Pelivanov et al., "NDT of fiber-reinforced composites with a new fiber-optic pump-probe laser-ultrasound system," Photoacoustics, vol. 2, Jan. 2014, 13 pages.

* cited by examiner

COMPOSITE INSPECTION

This application claims the benefit of U.S. Provisional Patent Application Ser. No. 62/270,546, filed Dec. 21, 2015, and entitled "Composite Inspection."

BACKGROUND INFORMATION

1. Field

The present disclosure relates generally to non-destructive inspection and, in particular, to performing non-destructive inspection on a layered structure. Still more particularly, the present disclosure relates to a method and apparatus for detecting wrinkles or compaction inconsistencies in a composite structure.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Non-destructive testing is commonly performed on these parts. Non-destructive testing is used to evaluate the properties of a part without altering the ability to use the part in service.

Ultrasound testing is a type of non-destructive testing. Ultrasound testing is often used to perform inspections on aircraft parts that include, or are comprised of, composite materials. Ultrasound testing involves transmitting acoustic waves through a test object, such as an aircraft part or structure.

Ultrasound testing is commonly performed using a transducer. The transducer is configured to send acoustic waves with the use of a coupling agent into a test object and detect a response to the acoustic waves. The response to these acoustic waves is analyzed to determine whether inconsistencies are present in the test object.

Aircraft, cars, medical devices, and even clothing are being designed and manufactured with greater and greater percentages of composite materials. For example, composite materials are used in aircraft to decrease the weight of the aircraft. This decreased weight improves performance features such as payload capacity and fuel efficiency. Further, composite materials provide longer service life for various components in an aircraft. Composite materials may also decrease the weight of other items such as artificial limbs, bicycles, cars, body armor, or other desirable products.

Composite materials may be tough, light-weight materials created by combining two or more functional components. For example, a composite material may include reinforcing fibers bound in a polymer resin matrix. Resins used in composite materials may include thermoplastic or thermoset resins. The fibers may be unidirectional or may take the form of a woven cloth or fabric.

In manufacturing composite structures, layers of composite material are typically laid up on a tool. The layers may be comprised of fibers in sheets. These sheets may take the form of fabrics, tape, tows, or other suitable forms. In some cases, resin may be infused or preimpregnated into the sheets. These types of sheets are commonly referred to as prepreg. The different layers of prepreg may be laid up in different orientations, and different numbers of layers may be used depending on the performance requirements of the composite structure being manufactured.

Inconsistencies may be introduced to the composite structure during manufacturing or during use of the composite structure. Due to the regular spacing of the layers that make up the composite material, inspection of the composite material may be more difficult than desired for some locations or some types of inconsistencies.

Further, some inconsistencies may not be conventionally detectable using conventional non-destructive techniques. Therefore, it would be desirable to have a method and apparatus that take into account at least some of the issues discussed above, as well as other possible issues.

SUMMARY

In one illustrative embodiment, a method of detecting inconsistencies in a composite structure is presented. A pulsed laser beam is directed towards the composite structure comprised of a number of composite materials. Wide-band ultrasonic signals are formed in the composite structure when radiation of the pulsed laser beam is absorbed by a surface of the composite structure. The wide-band ultrasonic signals are detected over a duration of time to form data. The data comprises an ultrasonic A-scan. The data is processed to identify a structure signal in a frequency domain of the ultrasonic A-scan. The structure signal of the ultrasonic A-scan is compared to a structure signal of a composite structure standard to determine whether the inconsistencies are present in the number of composite materials.

In another illustrative embodiment, a method is presented. A pulsed laser beam is directed towards a composite structure comprised of a plurality of layers. A number of wide-band ultrasonic signals are formed in the composite structure when radiation of the pulsed laser beam is absorbed by a surface of the composite structure. The wide-band ultrasonic signals are detected over a duration of time to form data. The data comprises a plurality of ultrasonic A-scans for the composite structure. A moving window is applied in a time domain to each of the plurality of ultrasonic A-scans. A frequency measurement is determined within the moving window for each of the plurality of ultrasonic A-scans. A structure signal is determined in the frequency domain of each ultrasonic A-scan spectrum of the plurality of ultrasonic A-scans using the frequency measurement. The structure signal of each ultrasonic A-scan spectrum of the plurality of ultrasonic A-scans is compared to a structure signal for the composite structure standard to form a plurality of comparisons.

In a further illustrative embodiment, a method is presented. Data is obtained for a composite structure using a laser ultrasound system. A width and a frequency of a structure signal in the data are determined. The structure signal from the data is compared to a structure signal of a composite structure standard to form a comparison. It is determined whether inconsistencies are present based on the comparison.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that the performance of composite structures depend on both composition and fabrication quality. The illustrative embodiments further recognize and take into account that composite materials may have reduced strength without any visually evident inconsistencies.

Further, the illustrative embodiments recognize and take into account that currently, wrinkles and compaction inconsistencies may be more difficult or more costly to detect than desired. For example, at least one of physical sectioning, polishing, micrography, wrinkle measurement (length over depth (L/D) and depth over thickness (D/t) may be used conventionally to characterize wrinkles. These values are tied to allowables and past correlations. It may be undesirably expensive to do all these steps, may take an undesirable amount of time, and the steps constitute destructive testing such that the part is scrapped.

Conventional ultrasonic characterization methods of wrinkles use B-scan images and reconstruction of return paths from reflections off of plies. This is done with time-based analysis. However, signals created by wrinkles are below the threshold for rejection. Accordingly, wrinkles must be found using human experience and human knowledge of wrinkle geometry. Further, because of potential differences from operator to operator, measurement of wrinkle shape may not be done repeatably and with a desired level of confidence.

Figure 1:
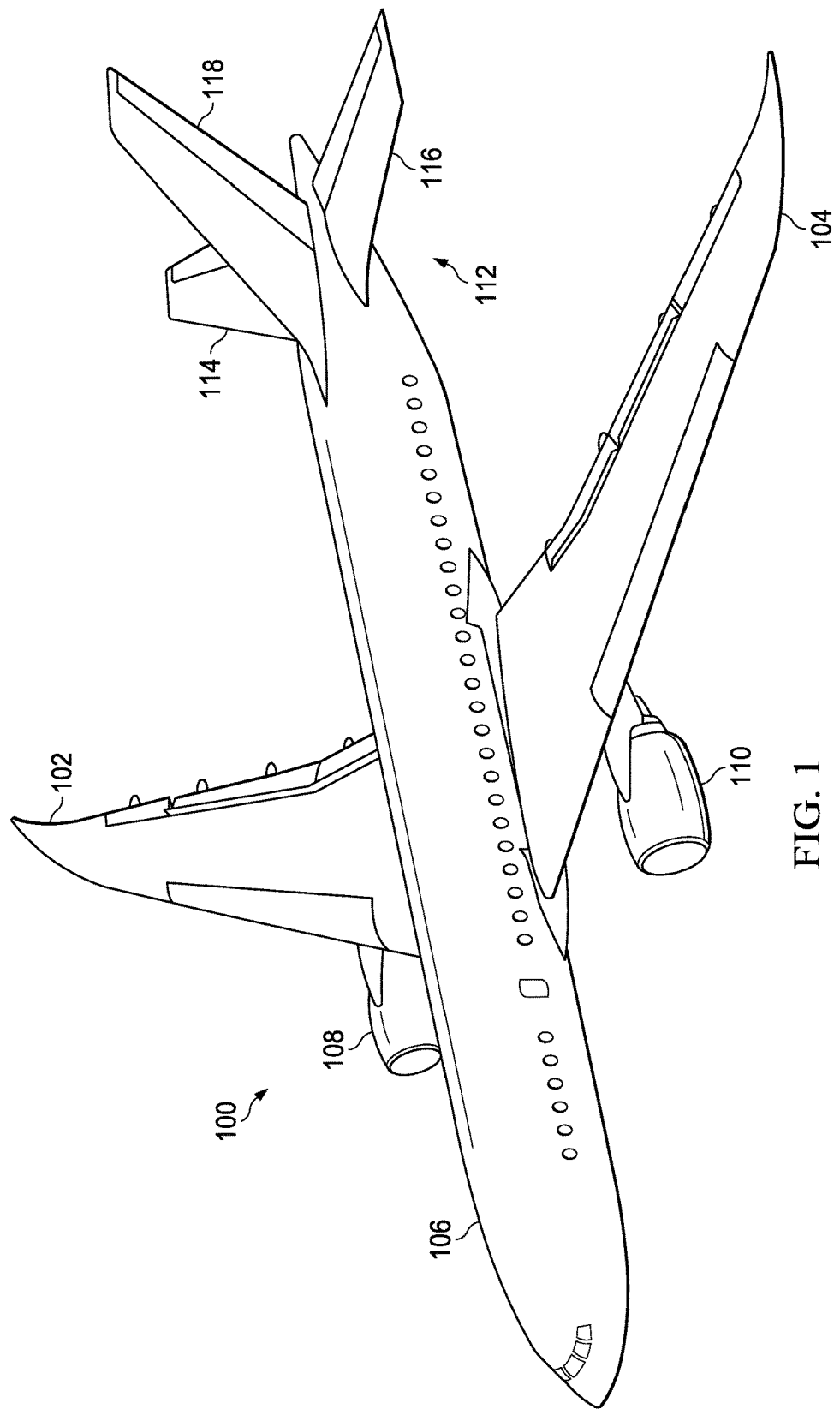
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106.

Aircraft 100 is an example of an aircraft having composite structures that may be inspected with a laser ultrasound inspection system in accordance with an illustrative embodiment. For example, composite skin in at least one of wing 102 or wing 104 may be inspected using a laser ultrasound inspection system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, an illustrative embodiment may be applied to other types of composite structures. For example, composite structures other than platforms may be inspected using a laser ultrasound inspection system. Composite structures other than platforms may include medical devices, prosthetic limbs, or any other desirable products for the screening, diagnosis, treatment, or prevention or any combination or sub-combination thereof of physical or mental health conditions in human beings or animals.

Figure 2:
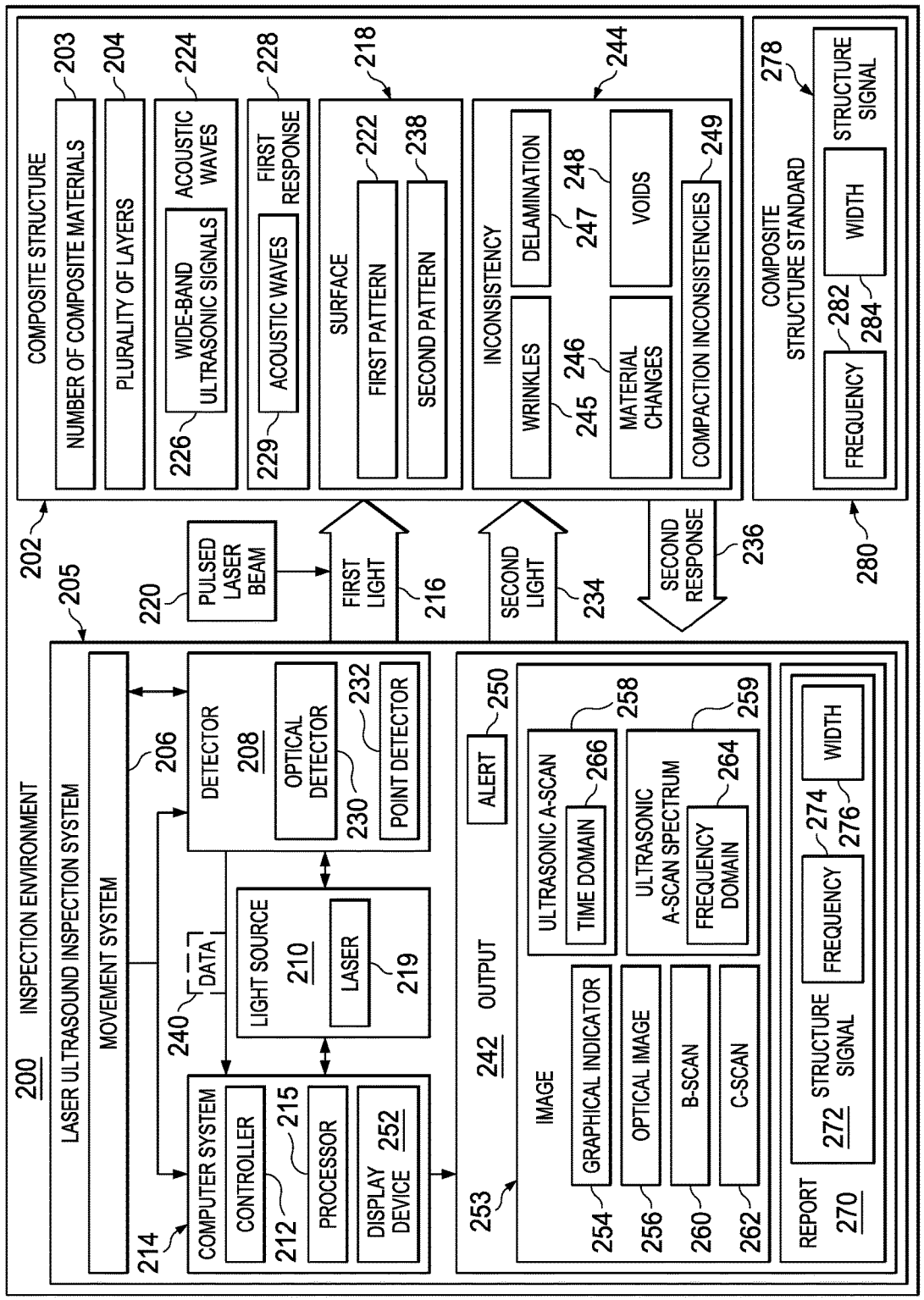
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. As depicted, inspection environment 200 includes composite structure 202. Composite structure 202 may take any number of forms. For example, composite structure 202 may be a part for an aircraft. Composite structure 202 is comprised of number of composite materials 203. Further, composite structure 202 is formed of plurality of layers 204. In some illustrative examples, plurality of layers 204 have a substantially consistent thickness and spacing.

In these illustrative examples, composite structure 202 is a composite part for an aircraft selected from one of a panel, a fuselage barrel, a stringer, a spar, a rib, a wing box, a wing, a stabilizer, and other suitable types of parts. Composite structure 202 is inspected using laser ultrasound inspection system 205. As depicted, laser ultrasound inspection system 205 includes movement system 206, detector 208, light source 210, and controller 212.

In these illustrative examples, controller 212 controls the operation of laser ultrasound inspection system 205. Controller 212 may be implemented using hardware, software, firmware, or a combination thereof.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the controller may be implemented using, for example, without limitation, program code configured to run on a processor unit, such as processor 215. When firmware is used, the operations performed by the controller may be implemented using, for example, without limitation, program code and data and stored in persistent memory to run on a processor unit.

When hardware is employed, the hardware may include one or more circuits that operate to perform the operations performed by the controller. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by the controller may be performed using organic components integrated with inorganic components. In some cases, the operations and/or processes may be performed by entirely organic components, excluding a human being. As one illustrative example, circuits in organic semiconductors may be used to perform these operations and/or processes.

Movement system 206 is configured to move light source 210 and detector 208 relative to composite structure 202. Movement system 206 is implemented using a number of different types of systems. For example, movement system 206 may be a robot. The robot may be, for example, a robotic arm that may move detector 208 about a number of axes. Movement system 206 also may be, for example, without limitation, a gantry robot, a hand-operated scanning head, and other suitable types of movement systems.

Light source 210 is configured to transmit first light 216 onto surface 218 of composite structure 202. In some illustrative examples, light source 210 is laser 219. More specifically, laser 219 may be a diode-pumped nanosecond laser. When light source 210 takes the form of laser 219, first light 216 may be pulsed laser beam 220.

In this illustrative example, first light 216 is transmitted in a manner that forms first pattern 222 on surface 218 of composite structure 202. In these illustrative examples, first pattern 222 of first light 216 is a plurality of areas on which first light 216 illuminates on surface 218. These areas may be circular, oval, square, oblique, or have some other shape depending on the angle of projection onto the surface. In some illustrative examples, first pattern 222 takes the form of a line.

First light 216 is configured to generate acoustic waves 224 within composite structure 202 when first light 216 encounters composite structure 202. Acoustic waves 224 occur when first light 216 is transmitted onto surface 218 of composite structure 202. For example, energy in first light 216 causes thermoelastic expansion in composite structure 202. The thermoelastic expansion results in the formation of acoustic waves 224 in composite structure 202.

In these illustrative examples, acoustic waves 224 are ultrasound sound waves. Thus, acoustic waves 224 may be ultrasonic signals when recorded by a receiving device. More specifically, acoustic waves 224 may take the form of wide-band ultrasonic signals 226. Wide-band ultrasonic signals 226 may have bandwidth greater than or equal to 50%. In these examples, the range of frequencies in a pulse is >=50% of the characteristic frequency of the pulse.

Acoustic waves 224 may have, for example, a frequency from about 20 kilohertz to about 100 megahertz depending on the particular implementation. The frequency for acoustic waves 224 may depend on the material used to form composite structure 202, the pulse width of the laser excitation, and other suitable factors.

Additionally, detector 208 is configured to detect first response 228 to acoustic waves 224. First response 228 includes acoustic waves 229 that occur as a result of scattering, reflection, modulation, and other changes to acoustic waves 224 traveling within composite structure 202. First response 228 is comprised of acoustic waves 229 that occur in response to acoustic waves 224. In this illustrative example, first response 228 is detected by detector 208.

In one illustrative example, detector 208 takes the form of optical detector 230. In some illustrative examples, detector 208 is point detector 232. In one example, detector 208 comprises any form of interferometer. For example, detector 208 may include a fiber-optic modified Sagnac interferometer for non-contact detection of backscattered ultrasound.

Detector 208 transmits second light 234 onto surface 218 of composite structure 202 and detect second response 236 to second light 234.

In one illustrative example, second light 234 is transmitted in the form of second pattern 238 onto surface 218 of composite structure 202. In this illustrative example, second pattern 238 takes the form of a point.

Second response 236 is second light 234 that has been deflected by first response 228 in this illustrative example. First response 228, caused by acoustic waves 224 traveling within composite structure 202, reaches surface 218 and is detected. The detection of first response 228 may be detected using an interferometer that sends a reference light, such as second light 234 and detects the mechanical vibrations on surface 218 in second response 236. Detector 208 may include any desirable form of interferometer.

Detector 208 sends data 240 to controller 212 when second response 236 is detected. Data 240 is used by controller 212 to generate output 242. In some examples, data 240 includes a full-bandwidth signal for a location of composite structure 202 being inspected. When data 240 includes received signals for a plurality of locations of composite structure 202, data 240 includes a plurality of ultrasonic A-scans. As laser ultrasound inspection system 205 is scanned across composite structure 202, data 240 for a plurality of locations on composite structure 202 is collected.

As depicted, output 242 indicates whether inconsistency 244 is present in composite structure 202. Inconsistency 244 may be, for example, without limitation, at least one of wrinkles 245, material changes 246, delamination 247, voids 248, compaction inconsistencies 249 or other undesired features or properties in composite structure 202.

Output 242 takes any desirable form. In one example, output 242 takes the form of alert 250. Alert 250 indicates whether inconsistency 244 is present. Alert 250 may be displayed on display device 252 within computer system 214.

In another illustrative example, output 242 is image 253. Image 253 also may be displayed on display device 252. When inconsistency 244 is present in composite structure 202, Image 253 is an image of a portion or all of composite structure 202 with graphical indicator 254. In some examples, graphical indicator 254 is displayed in a location in image 253 corresponding to a location in composite structure 202 where inconsistency 244 is detected. In other illustrative examples, if inconsistency 244 is absent, graphical indicator 254 may be displayed to indicate an absence of inconsistency 244.

In some illustrative examples, image 253 is optical image 256. Optical image 256 is an image of surface 218 of composite structure 202.

In other illustrative examples, image 253 is a representation of a portion of composite structure 202. For example, image 253 may be ultrasonic A-scan 258, ultrasonic A-scan spectrum 259, B-scan 260, or C-scan 262. Ultrasonic A-scan 258 and ultrasonic A-scan spectrum 259 are each a graph. Ultrasonic A-scan spectrum 259 is displayed in frequency domain 264. Ultrasonic A-scan spectrum 259 is computed by Fourier transform of ultrasonic A-scan 258. Ultrasonic A-scan 258 is in time domain 266. Ultrasonic A-scan 258 in time domain 266 is obtained by performing an inverse Fourier transform on ultrasonic A-scan spectrum 259 in frequency domain 264. In some examples, frequency domain 264 has an x-axis of frequency and a y-axis of amplitude. In some examples, time domain 266 has an x-axis of time and a y-axis of amplitude.

In some illustrative examples, ultrasonic A-scan 258 is a representation of data 240. As a result, data 240 may be said to include ultrasonic A-scan 258. In other illustrative examples, ultrasonic A-scan 258 is a representation of a portion of data 240 after data 240 is processed.

Ultrasonic A-scan 258 is representative of a location of composite structure 202. Data from ultrasonic A-scan 258 is combined with data from a plurality of ultrasonic A-scans of different locations of composite structure 202 to form B-scan 260. B-scan 260 may be at least one of a color or a grayscale image. In other examples, B-scan 260 may be a color image. The value of each pixel in B-scan 260 is representative of an intensity of second response 236 of a corresponding location of composite structure 202.

In one example, B-scan 260 has an x-axis of scanning distance and a y-axis of time. B-scan 260 may be a representation of data 240 or a representation of data 240 after data 240 is processed.

C-scan 262 is representative of all or a portion of composite structure 202. In one example, C-scan 262 has the same two-dimensional shape as all or a portion of composite structure 202. In some illustrative examples, C-scan 262 is a grayscale image. In other illustrative examples, C-scan 262 is a color image. The value of each pixel in C-scan 262 is representative of any desirable information. In one example, the value of each pixel in C-scan 262 is representative of locations of inconsistency 244 in composite structure 202. More specifically, the value of each pixel in C-scan 262 may be representative of locations of compaction inconsistencies 249 or wrinkles 245 in composite structure 202.

In another illustrative example, image 253 takes the form of frequency image 268. Frequency image 268 is similar to B-scan 260 in the x-axis and y-axis type. For example, frequency image 268 may have an x-axis of scanning distance and a y-axis of time. However, the intensity of each pixel in frequency image 268 is indicative of a frequency such as a mean frequency or a max frequency determined by processing data 240. Frequency image 268 indicates the presence of inconsistencies 244 in a portion of composite structure 202 represented in frequency image 268.

In still another illustrative example, output 242 takes the form of report 270. Report 270 may identify any inconsistencies in composite structure 202. Report 270 also may include other information, such as locations of inconsistencies, types of inconsistencies, sizes of inconsistencies, and other suitable types of information.

In some illustrative examples, report 270 includes structure signal 272. Structure signal 272 includes frequency 274 and width 276. In some illustrative examples, report 270 presents structure signal 272 as a graph. In some illustrative examples, report 270 presents alphanumeric values of frequency 274 and width 276 for structure signal 272. Structure signal 272 as used herein, is a signal in the frequency domain that may be affected by bulk material properties in the structure.

Structure signal 272 is compared to structure signal 278 of composite structure standard 280. Composite structure standard 280 has the same layup and materials as composite structure 202. Composite structure standard 280 is verified to have desirable structural properties.

Structure signal 278 includes frequency 282 and width 284. If frequency 274 differs from frequency 282, inconsistency 244 may be present. More specifically, if frequency 274 differs from frequency 282, at least one of wrinkles 245 or compaction inconsistencies 249 may be present. If width 276 differs from width 284, wrinkles 245 may be present. More specifically, width 276 may be broader than width 284 when wrinkles 245 are present. In some illustrative examples, porosity such as voids 248 may affect one of frequency 282 or width 284. Thus, output 242 may be at least one of alert 250, image 253, report 270, or other suitable types of output.

The illustration of inspection environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although inspection environment 200 includes composite structure 202, in some illustrative examples, inspection environment 200 instead includes a structure of any desirable material. For example, inspection environment 200 includes a structure made from any desirable material with a plurality of layers.

Figure 3:
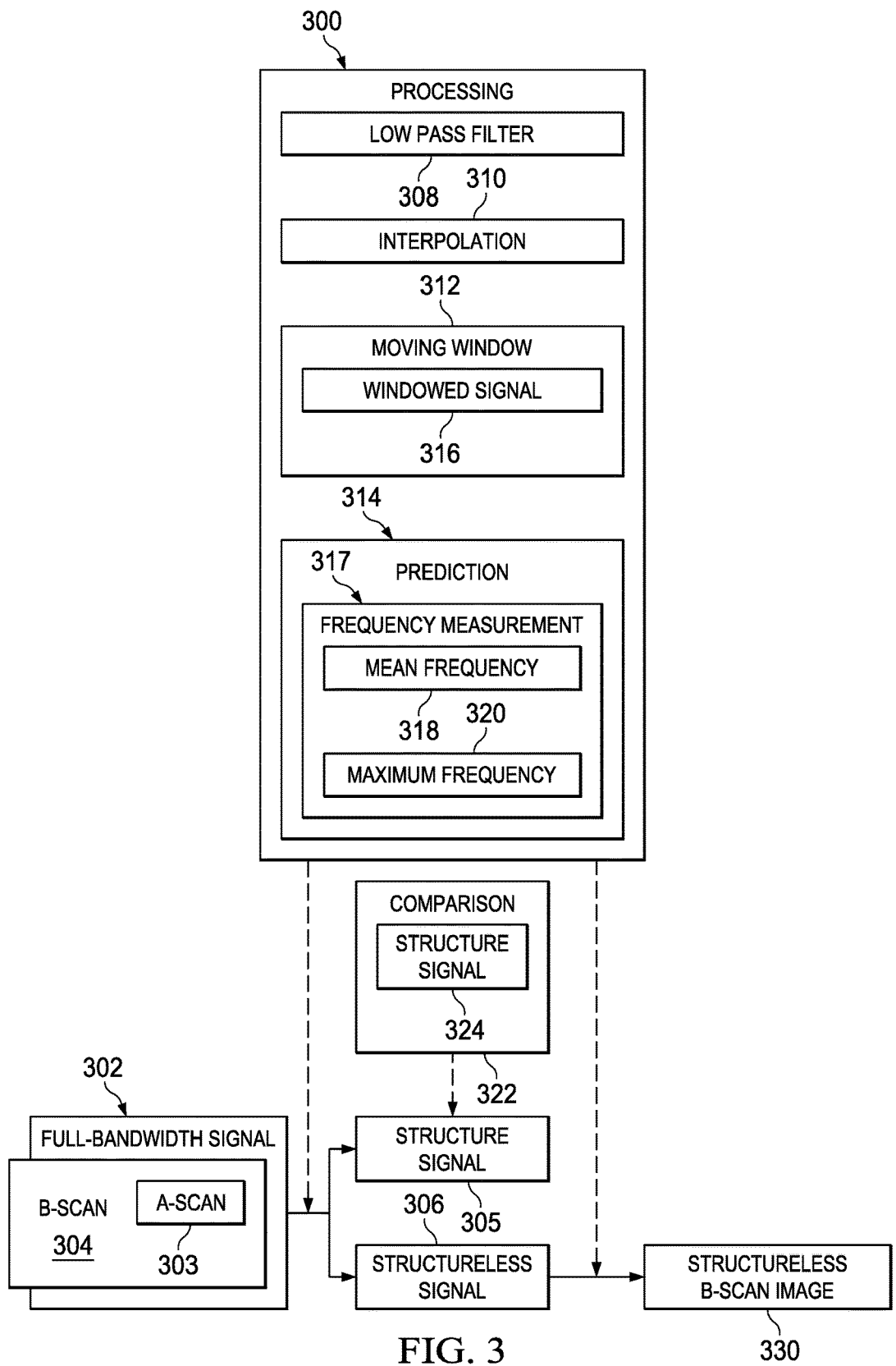
FIG. 3 is an illustration of a block diagram of processing of detector data in accordance with an illustrative embodiment.

Turning now to FIG. 3, an illustration of a block diagram of processing of detector data is depicted in accordance with an illustrative embodiment. Processing 300 of full-bandwidth signal 302 may be performed in computer system 214 of FIG. 2. Full-band width signal 302 may be the data collected by detector 208. The detector used may limit the bandwidth in Full-bandwidth signal 302. In one illustrative example, the detector bandwidth maximum may be 10 MHz. A detector may be selected such that an expected structure signal is positioned in full-bandwidth signal 302. For example, if an expected structure signal is approximately 7 MHz, the detection bandwidth should be higher than 7 MHz. Processing 300 of full-bandwidth signal 302 may be performed by processor 215 of FIG. 2.

Full-bandwidth signal 302 may be all or part of data 240 of FIG. 2. In some illustrative examples, full-bandwidth signal 302 is referred to as A-scan 303. A-scan 303 is a portion of B-scan 304. B-scan 304 includes further A-scans other than A-scan 303. A-scan 303 is data for a first location on a composite structure. The further A-scans of B-scan 304 include other locations of the same composite structure.

Full-bandwidth signal 302 undergoes processing 300 to create one of structure signal 305 or structureless signal 306. Structure signal 305 is used to determine whether inconsistencies, such as wrinkles 245 or compaction inconsistencies 249 of FIG. 2, are present in a structure with a plurality of regular layers. Structureless signal 306 increases detection of macroscopic inconsistencies in a structure with a plurality of layers. Structureless signal 306 depicts a clearer image of inconsistencies.

Processing 300 includes any desirable series of operations. In this example, processing 300 includes at least one of low pass filter 308, interpolation 310, moving window 312, or prediction 314. The desirable series of operations of processing 300 are performed in any desirable order.

In one illustrative example, processing 300 on full-bandwidth signal 302 to form structure signal 305 includes moving window 312 and then prediction 314. In some illustrative examples, moving window 312 is a filter. Moving window 312 is applied to A-scan 303 in a time domain.

Moving window 312 is applied to full-bandwidth signal 302 such that only a few cycles of full-bandwidth signal 302 are contained within moving window 312 during a period of time. In some illustrative examples, moving window 312 is a Gaussian shape. The Gaussian shape provides an advantageous tradeoff between frequency resolution and time resolution. Frequency resolution provides for precise removal and interpolation in the frequency domain. Time resolution provides for spatial resolution in a frequency image.

Moving window 312 is described in terms of sampling size or time. A minimum window size for moving window 312 is the duration of the interrogating pulse. Moving window 312 is typically larger than this duration to get better spectral resolution in the frequency domain. Duration in time domain is inversely proportional to resolution in frequency domain. The choice of characteristics for moving window 312 is determined by a tradeoff between required resolution in the frequency domain and required resolution in the time domain. As discussed above, a Gaussian shape may optimize this tradeoff.

Moving window 312 is sized such that moving window 312 only contains cycles from a desired number of plies. In one example, moving window 312 length contains cycles from any desirable number of plies from two to seven plies. For example, moving window 312 contains cycles from three plies. In another example, moving window 312 contains cycles from five plies.

In one illustrative example, moving window 312 has a diameter of 100 samples where the sampling frequency is 200 MHz and the speed of sound propagation is such that 30 samples contain the response from one ply. Thus, in this example, a windowed signal contains only a few plies.

Each time moving window 312 is applied to full-bandwidth signal 302, windowed signal 316 is formed. For each windowed signal, prediction 314 may be performed. Prediction 314 determines frequency measurement 317. In one illustrative example, frequency measurement 317 is mean frequency 318. In another illustrative example, frequency measurement 317 is maximum frequency 320. Prediction 314 determines structure signal 305 using at least one of mean frequency 318 or maximum frequency 320.

Mean frequency 318 is determined using any desirable equation. Mean frequency 318 is determined for each windowed signal 316 of full-bandwidth signal 302. Further, mean frequency 318 is determined for other full-bandwidth signals other than full-bandwidth signal 302. For example, mean frequency 318 is determined for each windowed signal 316 of each A-scan of B-scan 304. In one example, for a given frequency range the mean frequency in the windowed signal is determined using the power spectrum given by the following equation:

$$f_{mean} = \frac{\sum_{i=1}^{N} f_i P_i}{\sum_{i=1}^{N} P_i} \tag{1}$$

where N is the total number of bins in the frequency range, $f_i$ is the frequency at the frequency bin i and $P_i$ is the power at the frequency bin i.

Mean frequency 318 is used to identify a frequency of structure signal 305. A width of structure signal 305 is determined by any desirable method. For instance, in one example, the width is determined at the frequency for which the response drops by at least 6 dB, or for complex frequency spectrum curves a best fit can be applied using least-squares or a spline curve to calculate the full-width half-maximum (FWHM) of the fit.

When frequency measurement 317 is maximum frequency 320, maximum frequency 320 may be predicted using any desirable method. In one example, maximum frequency 320 is predicted using the following equation:

$$S_n = \Sigma_{k=1}^{P} \alpha_k * S_{n-k} \quad (2)$$

where $\alpha_k$ is a $k^{th}$ Fourier coefficient, p is a quantity of coefficients, $S_n$ is the A-scan signal at sample point n, and $S_{n-k}$ is the A-scan signal at prior sample point n-k.

Structure signal 305 is used to determine whether wrinkles or compaction inconsistencies are present in an area of a composite structure represented by B-scan 304. Determining if inconsistencies are present includes comparison 322. Comparison 322 compares structure signal 305 to structure signal 324 of a composite structure standard, such as composite structure standard 280 of FIG. 2. Inconsistencies are determined to be present if at least one of frequency or width of structure signal 305 differs from frequency or width of structure signal 324 of a composite structure standard.

For example, the width of structure signal 305 is broader than the width of structure signal 324 of the composite structure standard if compaction inconsistencies are present. As another example, the frequency of structure signal 305 differs from the frequency of structure signal 324 of the composite structure standard if at least one of a wrinkle or compaction inconsistencies are present.

In another illustrative example, processing 300 on full-bandwidth signal 302 creates structureless signal 306. For example, after determining structure signal 305, structure signal 305 is removed from full-bandwidth signal 302. Structureless signal 306 is used to form structureless B-scan image 330.

Figure 4:
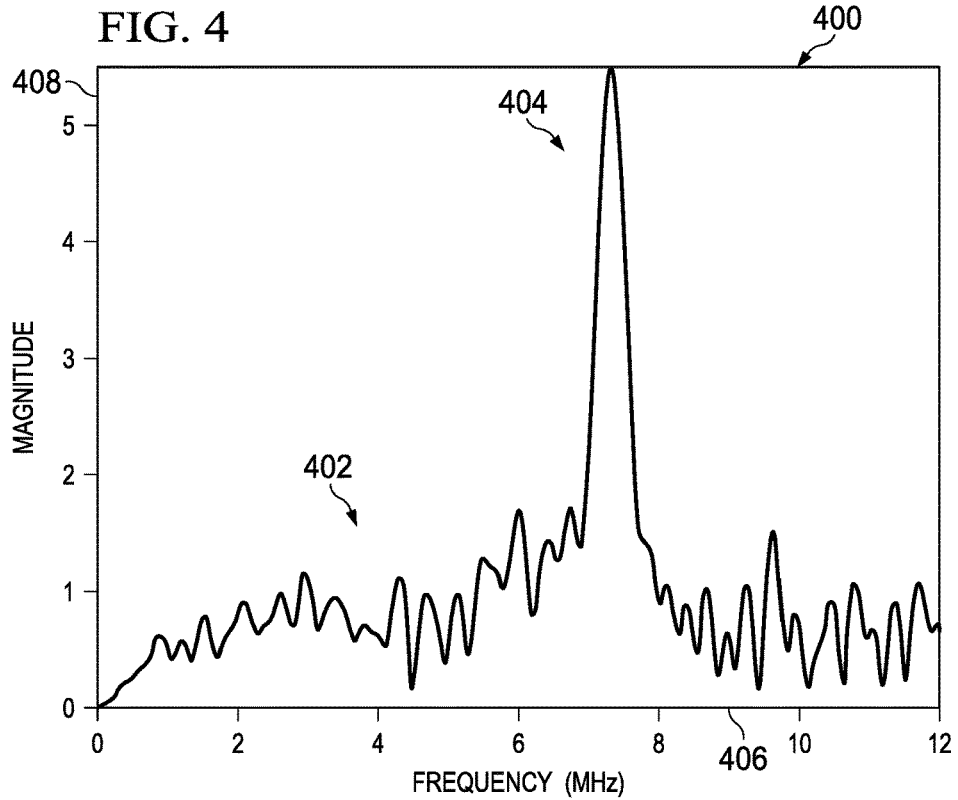
FIG. 4 is an illustration of an ultrasonic A-scan spectrum in the frequency domain in accordance with an illustrative embodiment.

Turning now to FIG. 4, an illustration of an ultrasonic A-scan in the frequency domain is depicted in accordance with an illustrative embodiment. Image 400 is a physical implementation of image 253 of FIG. 2. Image 400 includes A-scan spectrum 402. A-scan spectrum 402 in the frequency domain is computed from the Fourier Transform of the A-Scan. A-scan spectrum 402 is an example of ultrasonic A-scan spectrum 259 in frequency domain 264 of FIG. 2. A-scan spectrum 402 is a Fourier Transform of ultrasonic A-scan 258 in time domain 266.

A-scan spectrum 402 includes structure signal 404. Structure signal 404 is identified using a prediction. Image 400 has x-axis 406 and y-axis 408. In this example, A-scan spectrum 402 is in frequency domain. Accordingly, x-axis 406 is frequency in MHz and y-axis 408 is magnitude.

A-Scan spectrum 402 in FIG. 4 is presented in the frequency domain. The equivalent time domain representation as an A-Scan is obtained by inverse Fourier transforming A-Scan spectrum 402 in image 400.

Figure 5:
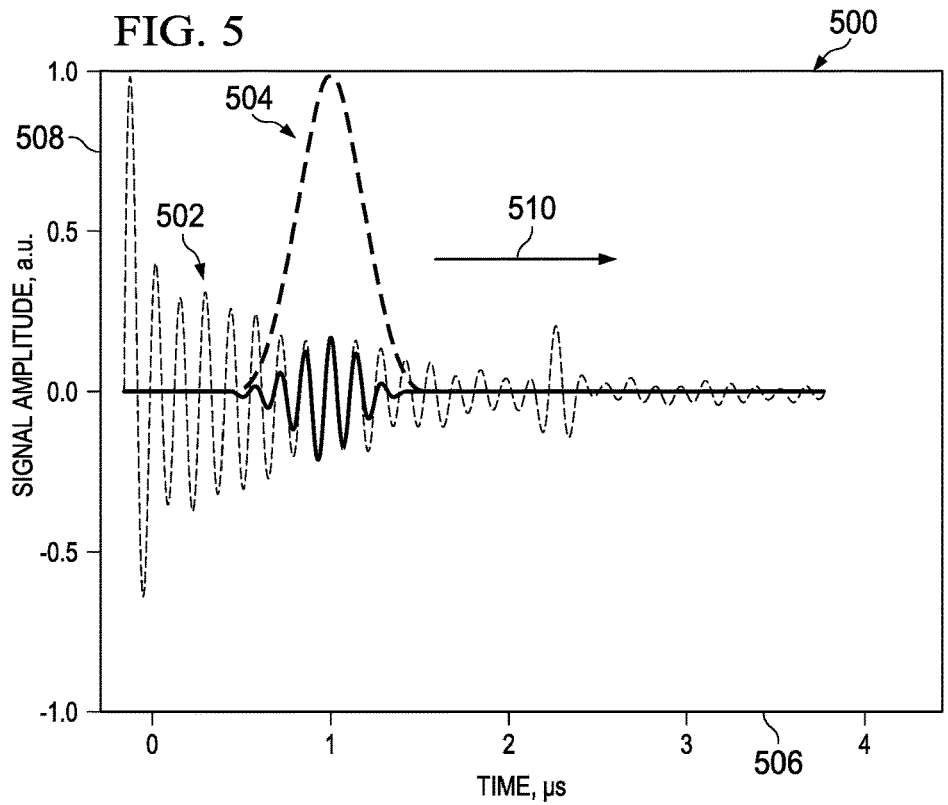
FIG. 5 is an illustration of a moving window on an ultrasonic A-scan in the time domain in accordance with an illustrative embodiment.

Turning now to FIG. 5, an illustration of a moving window on an ultrasonic A-scan in the time domain is depicted in accordance with an illustrative embodiment. Image 500 is a physical implementation of image 253 of FIG. 2. Image 500 includes A-scan 502. A-scan 502 is an example of ultrasonic A-scan 258 in time domain 266 of FIG. 2. Moving window 504 is positioned over A-scan 502.

Image 500 has x-axis 506 and y-axis 508. In this example, A-scan 502 is in a time domain. Accordingly, x-axis 506 is time in microseconds and y-axis 508 is amplitude.

Moving window 504 is applied to A-scan 502 to determine frequency measurements. Moving window 504 includes a number of plies of the composite structures. In this illustrative example, moving window 504 includes five plies for A-scan 502.

Moving window 504 is moved in direction 510 in image 500 to form a number of windowed signals. Frequency measurements are determined for each windowed signal of A-scan 502. The frequency measurements of A-scan 502 are used to determine whether material changes have occurred in the composite structure of A-scan 502. For example, the frequency measurements of A-scan 502 are used to form a frequency image.

In some illustrative examples, frequency measurements of A-scan 502 are used to increase the detectability of inconsistencies. For example, frequency measurements of A-scan 502 are used to predict the structure signal. The structure signal is then removed from the full-bandwidth signal. After removing the structure signal, an interpolation may be performed. The interpolated signal is then be used to form a B-scan.

Figure 6:
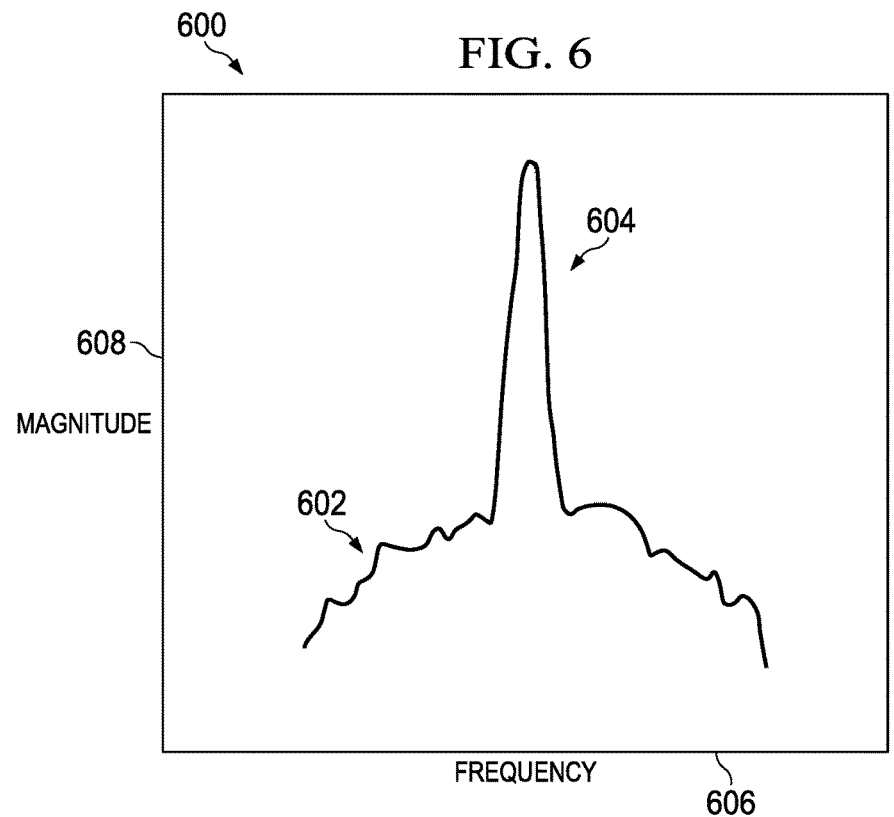
FIG. 6 is an illustration of a structure signal of a composite structure standard in the frequency domain in accordance with an illustrative embodiment.

Turning now to FIG. 6, an illustration of a structure signal of a composite structure standard in the frequency domain is depicted in accordance with an illustrative embodiment. Image 600 includes A-scan 602. A-scan 602 is an example of an ultrasonic A-scan in time domain 266 for composite structure standard 280 of FIG. 2.

A-scan 602 includes structure signal 604. Structure signal 604 is used in a comparison to structure signals taken from a composite structure to be tested. Structure signal 604 is a physical implementation of structure signal 278 of FIG. 2. Image 600 has x-axis 606 and y-axis 608. In this example, A-scan 602 is in frequency domain. Accordingly, x-axis 606 is frequency in MHz and y-axis 608 is magnitude.

Figure 7:
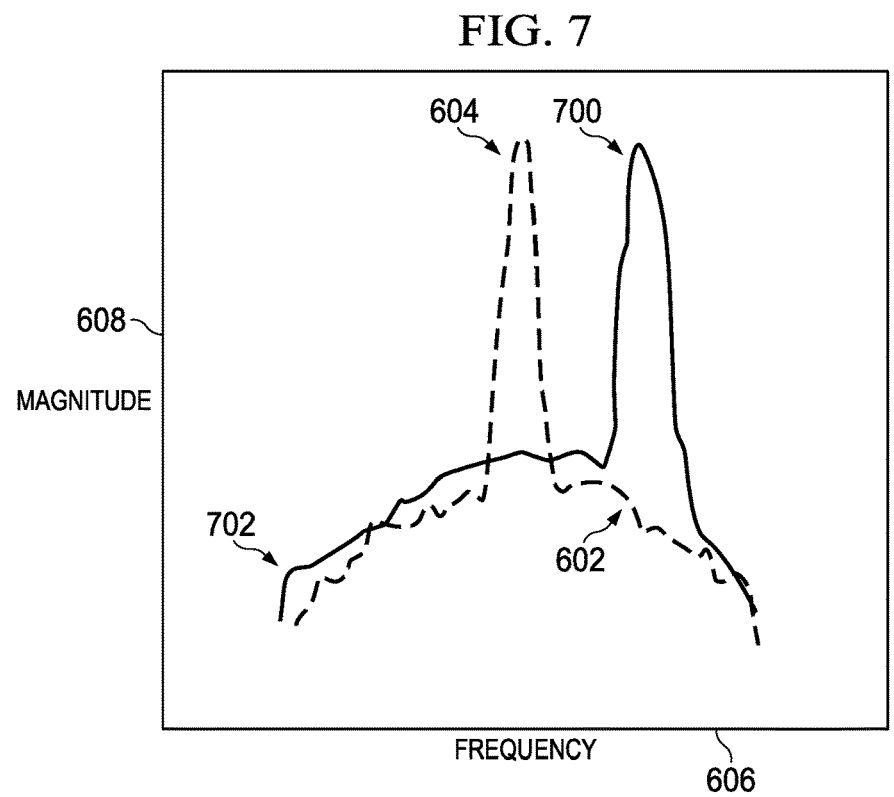
FIG. 7 is an illustration of an overlay of a structure signal for a composite structure and a structure signal of a composite structure standard in the frequency domain in accordance with an illustrative embodiment.

Turning now to FIG. 7, an illustration of an overlay of a structure signal for a composite structure and a structure signal of a composite structure standard in the frequency domain is depicted in accordance with an illustrative embodiment. Structure signal 700 is a physical implementation of structure signal 272. As depicted, structure signal 272 is noticeably shifted from structure signal 604 along x-axis 606. In other words, the frequency of structure signal 700 differs from the frequency of structure signal 604. As depicted, the composite structure has compaction inconsistencies in the location represented by A-scan 702. Frequency increases with increased compaction in the composite through the material traversed by the ultrasonic signal. For example, the compaction in the location represented by A-scan 702 is greater than the compaction in the composite structure standard. By quantifying the frequency of structure signal 700, the compaction at the sampling location is determined.

By quantifying the frequency at each location across a composite structure, the compaction of each location of the composite structure is determined. When the compaction at each location of composite structure is determined, the compaction may be mapped. For example, a C-scan is created to display the compaction levels across the composite structure.

Figure 8:
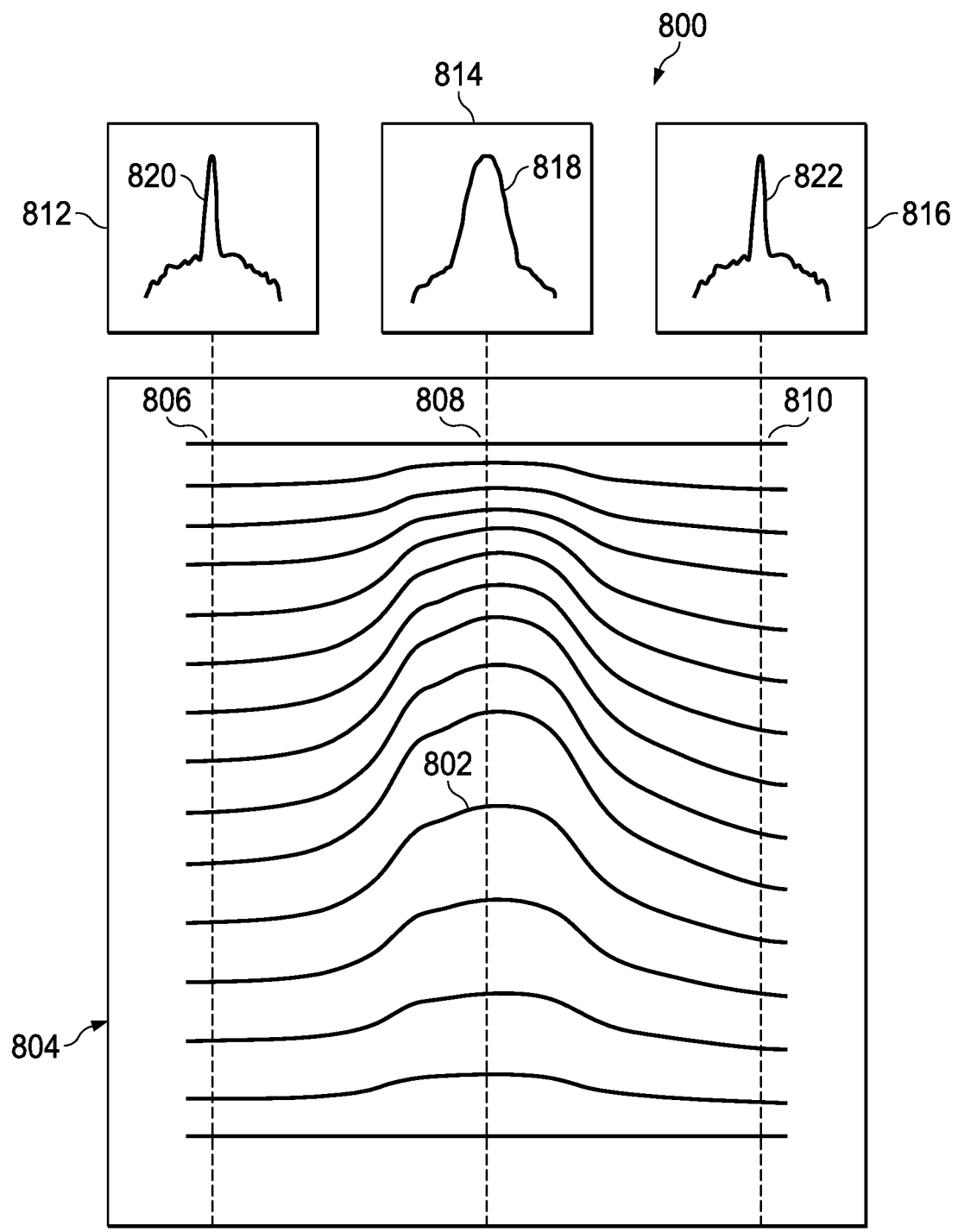
FIG. 8 is an illustration of a through thickness composite structure having a wrinkle and associated structure signals in the frequency domain in accordance with an illustrative embodiment.

Turning now to FIG. 8, an illustration of a through thickness composite structure having a wrinkle and associated structure signals in the frequency domain is depicted in accordance with an illustrative embodiment. Image 800 is a depiction of a slice through the thickness of composite structure 202 in FIG. 2. As depicted, wrinkle 802 is present in composite structure 804. Pulsed laser beams are directed at location 806, location 808, and location 810 of composite structure 804. Ultrasonic A-scan 812 may be data from location 806. Ultrasonic A-scan 814 is data from location 808. Ultrasonic A-scan 816 is data from location 810.

As can be seen in image 800, structure signal 818 in ultrasonic A-scan 814 has a greater width than the width of either structure signal 820 or structure signal 822. An increased or broadened width of a structure signal may be indicative of a wrinkle. The change in ply thickness over the depth of wrinkle 802 broadens the width of structure signal 818. To determine whether a wrinkle is present, each of structure signal 818, structure signal 820, and structure signal 822 are compared to a structure signal (not depicted) of a composite structure standard (not depicted). In some illustrative examples, the extent of the difference in width provides measurements as to the extent of wrinkle 802.

Figure 9:
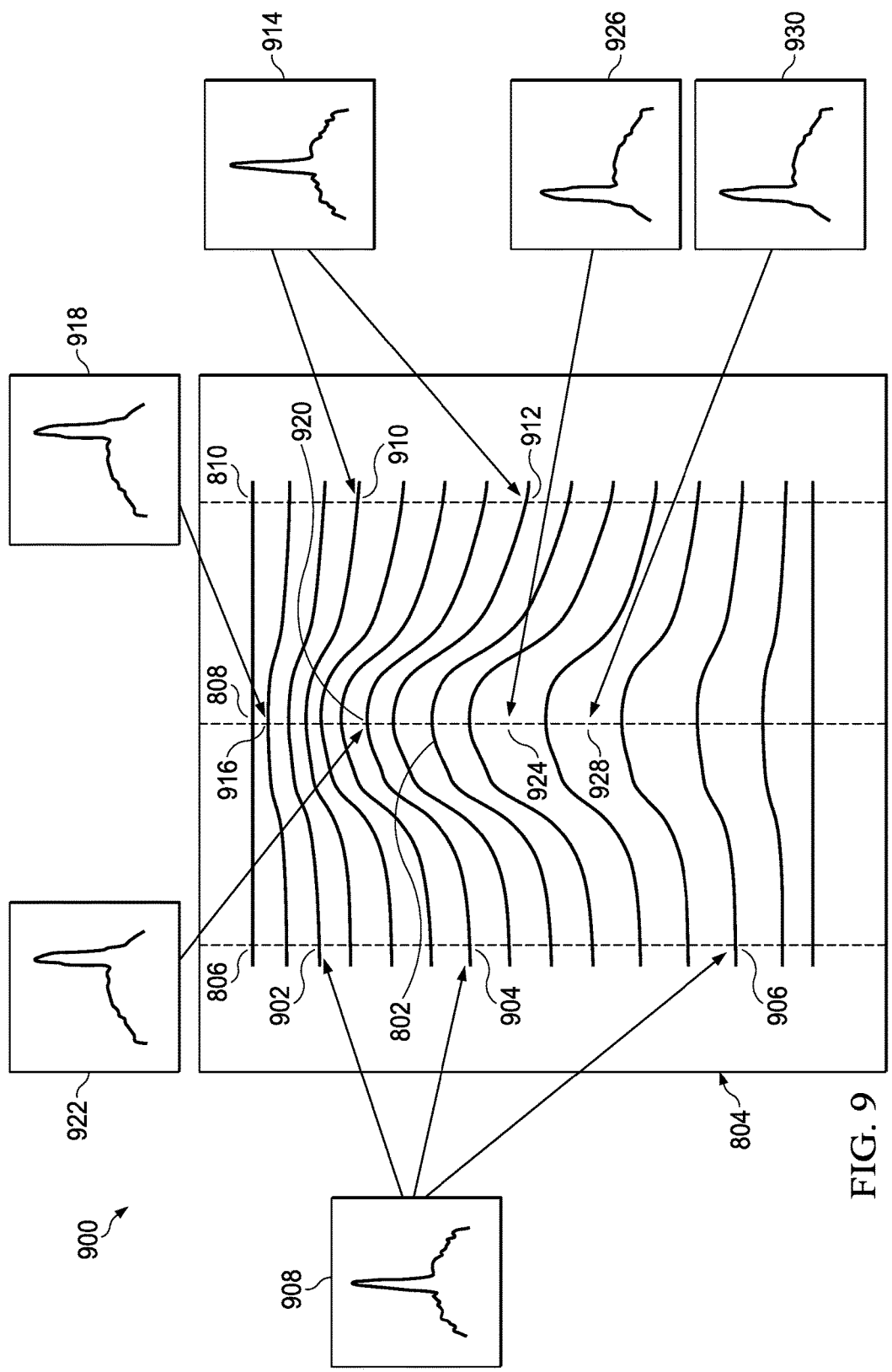
FIG. 9 is an illustration of a through thickness composite structure having a wrinkle and associated structure signals in the frequency domain in accordance with an illustrative embodiment.

Turning now to FIG. 9, an illustration of a through thickness composite structure having a wrinkle and associated structure signals in the frequency domain is depicted in accordance with an illustrative embodiment. Image 900 is a depiction of a slice through the thickness of composite structure 202 in FIG. 2. As depicted, wrinkle 802 is present in composite structure 804. Pulsed laser beams are directed at location 806, location 808, and location 810 of composite structure 804.

In image 900, A-scans are taken at a variety of depths along each of location 806, location 808, and location 810 of composite structure 804. For example, ultrasonic A-scans are substantially the same at depth 902, depth 904, and depth 906 at location 806. Accordingly, A-scan 908 resembles the A-scan for each of depth 902, depth 904, and depth 906 at location 806.

Likewise, ultrasonic A-scans are substantially the same at depth 910 and depth 912 at location 810. Accordingly, A-scan 914 resembles the A-scan for each of depth 910 and depth 912 at location 806. A-scan 908 and A-scan 914 are substantially the same.

However, ultrasonic A-scans may be different throughout location 808 due to wrinkle 802. Differing ultrasonic A-scans cause the broadening of width observed in structure signal 818 of FIG. 8. For example, at depth 916 at location 808, A-scan 918 is obtained. At depth 920 at location 808, A-scan 922 is obtained. At depth 924 at location 808, A-scan 926 is obtained. At depth 928 at location 808, A-scan 930 is obtained.

As can be seen in image 900, A-scan 926 and A-scan 930 are substantially different from A-scan 918 and A-scan 922. For example, the structure signal has shifted in frequency from A-scan 918 to A-scan 930. This shift in the frequency of the structure signal causes a broadening of the width of the structure signal throughout wrinkle 802.

Further, the frequency of the structure signal in each A-scan is compared to a frequency of a structure signal of a composite structure standard. For shifted frequencies, such as A-scan 918, A-scan 922, A-scan 926, and A-scan 930, compaction inconsistencies are present.

The different components shown in FIG. 1 and FIGS. 3-9 may be combined with components in FIG. 2, used with components in FIG. 2, or a combination of the two. Additionally, some of the components in FIG. 1 and FIGS. 3-9 may be illustrative examples of how components shown in block form in FIG. 2 may be implemented as physical structures.

Figure 10:
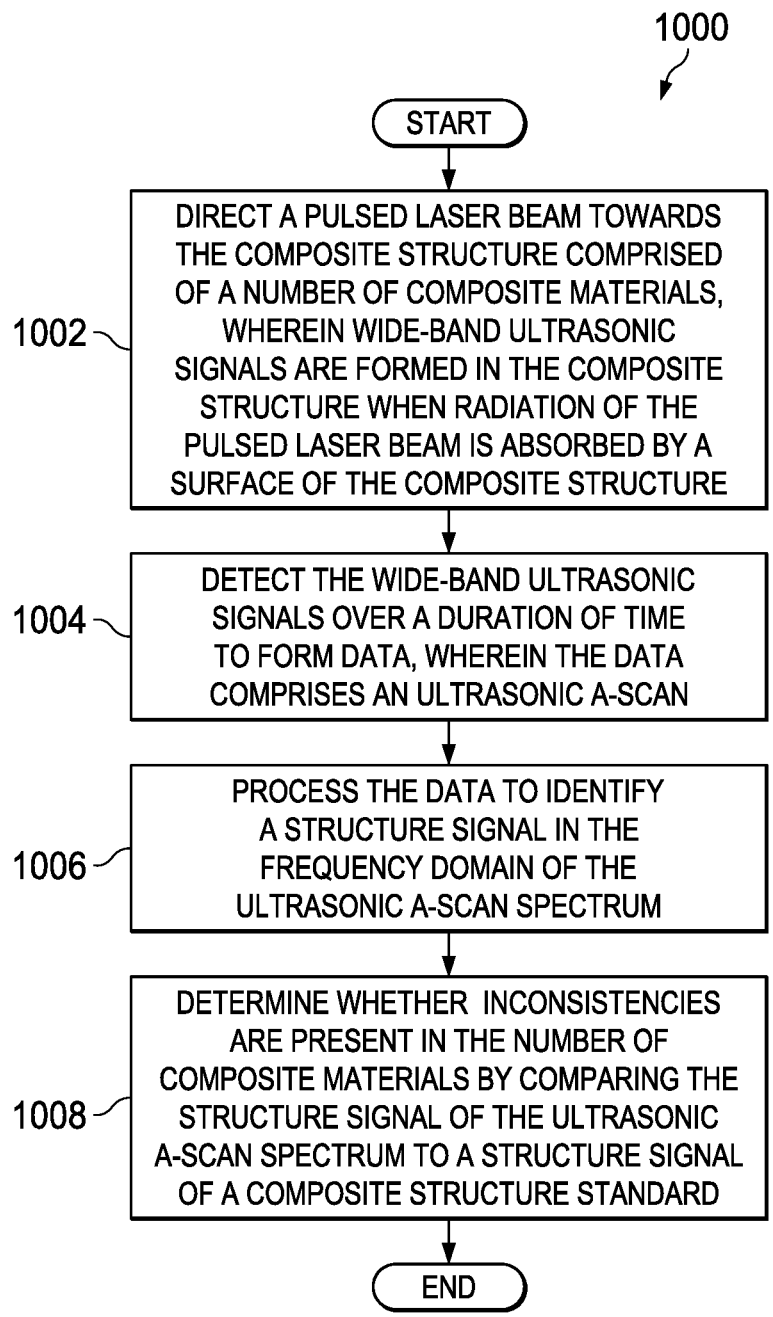
FIG. 10 is an illustration of a flowchart of a process for detecting inconsistencies in a composite structure in accordance with an illustrative embodiment.

Turning now to FIG. 10, an illustration of a flowchart of a process for detecting inconsistencies in a composite structure is depicted in accordance with an illustrative embodiment. The process illustrated in FIG. 10 may be implemented in an ultrasound inspection system such as laser ultrasound inspection system 205 in FIG. 2.

Process 1000 begins by directing a pulsed laser beam towards the composite structure comprised of a number of composite materials, wherein wide-band ultrasonic signals are formed in the composite structure when radiation of the pulsed laser beam is absorbed by a surface of the composite structure (operation 1002). Process 1000 then detects the wide-band ultrasonic signals over a duration of time to form data, wherein the data comprises an ultrasonic A-scan spectrum (operation 1004). In some illustrative examples, the wide-band ultrasonic signals are detected over a duration of time using a point-like optical detector of ultrasound. In some examples, the point-like optical detector of ultrasound is broadband.

Process 1000 also processes the data to identify a structure signal in the frequency domain of the ultrasonic A-scan spectrum (operation 1006). In some illustrative examples, processing the data comprises applying a moving window in the time domain to each of the ultrasonic A-scans to form windowed signals and determining at least one of a mean frequency or a maximum frequency of a Fourier spectrum taken for each of the windowed signals. The moving window may have a Gaussian shape.

In one illustrative example, processing the data comprises determining a maximum frequency of a windowed signal of an ultrasonic A-scan according to the following equation:

$$S_n = \Sigma_{k=1}^{P} \alpha_k * S_{n-k} \quad (3)$$

In this equation, $\alpha_k$ is a $k^{th}$ Fourier coefficient, p is a quantity of coefficients, $S_n$ is the A-scan signal at sample point n, and $S_{n-k}$ is the A-scan signal at prior sample point n-k.

Process 1000 further determines whether inconsistencies are present in the number of composite materials by comparing the structure signal of the ultrasonic A-scan spectrum to a structure signal of a composite structure standard (operation 1008). Afterwards, the process terminates.

In some illustrative examples, determining whether inconsistencies are present in the number of composite materials comprises determining whether a first width of the structure signal of the ultrasonic A-scan in the frequency domain differs from a second width of the structure signal of the composite structure standard in the frequency domain. In one example, determining whether inconsistencies are present in the number of composite materials further comprises determining a wrinkle is present in the number of composite materials if the first width differs from the second width.

In another illustrative example, determining whether inconsistencies are present in the number of composite materials comprises determining whether the structure signal of the ultrasonic A-scan is shifted in the frequency domain relative to the structure signal of the composite structure standard. In one example, determining whether inconsistencies are present in the number of composite materials further comprises determining compaction of the number of composite materials is undesirable if the structure signal of the ultrasonic A-scan is shifted in the frequency domain relative to the structure signal of the composite structure standard.

Figure 11:
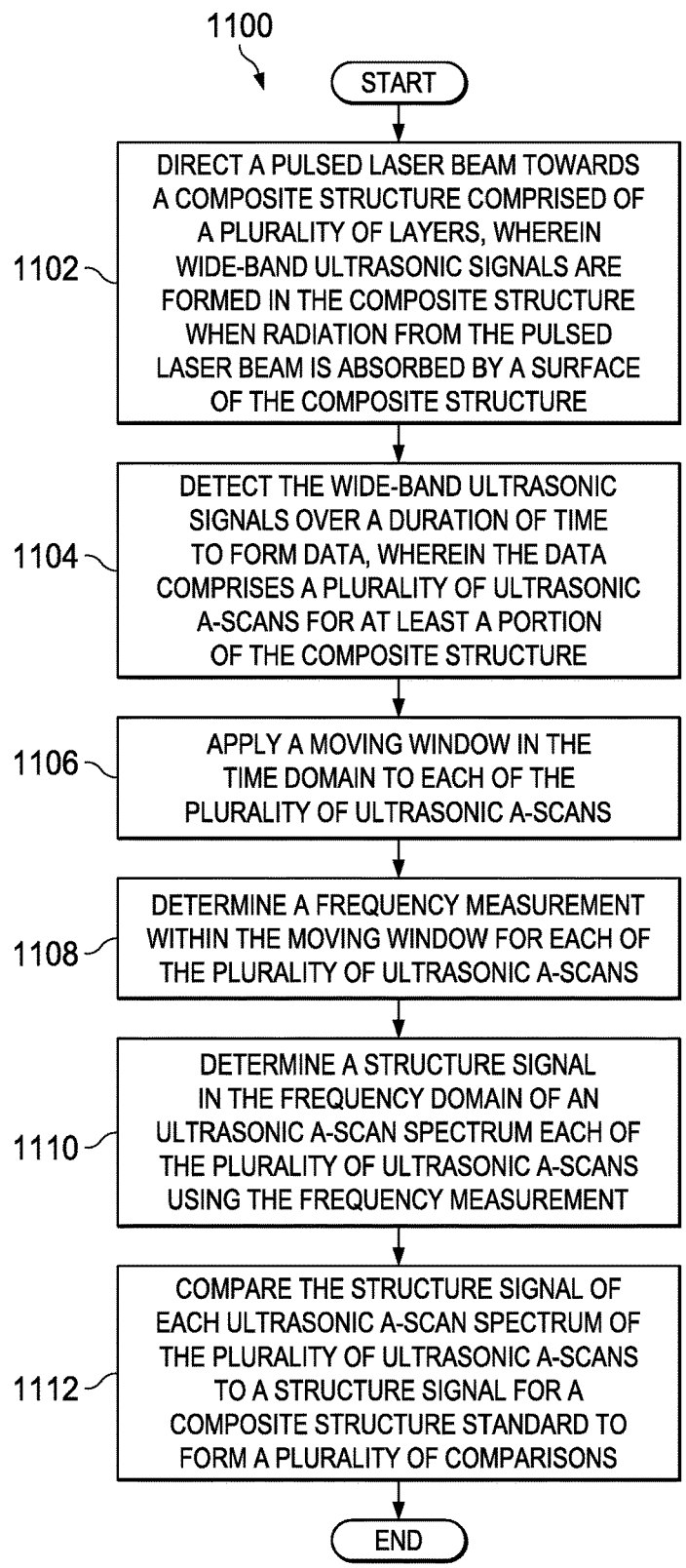
FIG. 11 is an illustration of a flowchart of a process for processing data to improve detection of inconsistencies in accordance with an illustrative embodiment.

Turning now to FIG. 11, an illustration of a flowchart of a process for processing data to improve detection of inconsistencies is depicted in accordance with an illustrative embodiment. The process illustrated in FIG. 11 may be implemented in an ultrasound inspection system such as laser ultrasound inspection system 205 in FIG. 2.

Process 1100 begins by directing a pulsed laser beam towards a composite structure comprised of a plurality of layers, wherein wide-band ultrasonic signals are formed in the composite structure when radiation of the pulsed laser beam is absorbed by a surface of the composite structure (operation 1102). Process 1100 also detects the wide-band ultrasonic signals over a duration of time to form data, wherein the data comprises a plurality of ultrasonic A-scans for at least a portion of the composite structure (operation 1104).

Process 1000 applies a moving window to each of the plurality of A-scans (operation 1106). Process 1000 determines a frequency measurement within the moving window for each of the plurality of A-scans (operation 1108). In some illustrative examples, the frequency measurement is selected from a mean frequency or a maximum frequency.

The maximum frequency may be determined according to the following equation:

$$S_n = \Sigma_{k=1}^{P} \alpha_k * S_{n-k} \qquad (4)$$

In this equation, p is a quantity of coefficients and $S_n$ is the A-scan signal at sample point n.

Process 1100 also determines a structure signal in the frequency domain of each ultrasonic A-scan spectrum of the plurality of ultrasonic A-scans using the frequency measurement (operation 1110). Process 1100 compares the structure signal of each ultrasonic A-scan spectrum of the plurality of ultrasonic A-scans to a structure signal for a composite structure standard to form a plurality of comparisons (operation 1112). Afterwards, the process terminates.

In some illustrative examples, comparing the structure signal of each ultrasonic A-scan spectrum of the plurality of ultrasonic A-scans to the structure signal of the composite structure standard comprises comparing a respective width of each structure signal of each respective ultrasonic A-scan spectrum of the plurality of ultrasonic A-scans to a width of the structure signal of the composite structure standard. In other illustrative examples, comparing the structure signal of each ultrasonic A-scan spectrum of the plurality of ultrasonic A-scans to the structure signal of the composite structure standard comprises comparing a respective location of each structure signal of each respective ultrasonic A-scan spectrum of the plurality of ultrasonic A-scans in the frequency domain to a location of the structure signal of the composite structure standard in the frequency domain.

Figure 12:
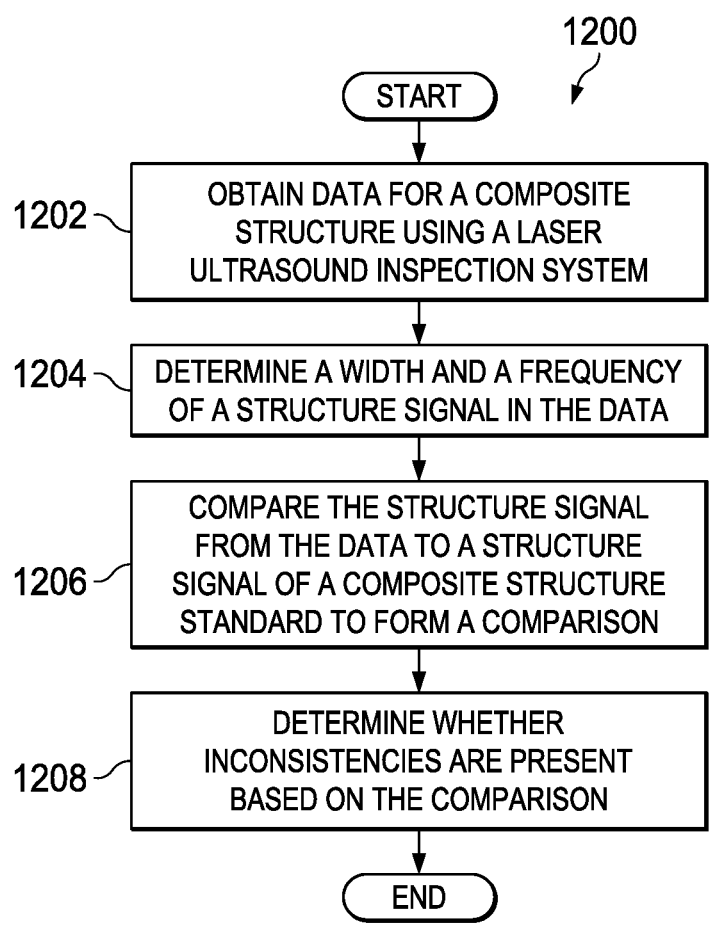
FIG. 12 is an illustration of a flowchart of a process for processing data to improve detection of inconsistencies in accordance with an illustrative embodiment.

Turning now to FIG. 12, an illustration of a flowchart of a process for processing data to improve detection of inconsistencies in accordance with an illustrative embodiment. The process illustrated in FIG. 12 may be implemented in an ultrasound inspection system such as laser ultrasound inspection system 205 in FIG. 2.

Process 1200 begins by obtaining data for a composite structure using a laser ultrasound inspection system (operation 1202). In some illustrative examples, the composite structure has a plurality of layers.

Process 1200 determines a width and a frequency of a structure signal in the data (operation 1204). In some illustrative examples, the frequency of the structure signal is determined using the following equation:

$$S_n = \Sigma_{k=1}^{P} \alpha_k * S_{n-k} \qquad (5)$$

where p is a quantity of coefficients and $S_n$ is the A-scan signal at sample point n.

The width of the structure signal may be determined by any desirable method. In one example, the width is determined at the frequency for which the response drops by at least 6 dB. In some illustrative examples, the width of the structure signal is determined by a best fit analysis. For example, for complex frequency spectrum curves, a best fit is applied using least-squares or a spline curve to calculate the full-width half-maximum (FWHM) of the fit.

Process 1200 compares the structure signal from the data to a structure signal of a composite structure standard to form a comparison (operation 1206). Process 1200 then determines whether inconsistencies are present based on the comparison (operation 1208). Afterwards the process terminates. In one illustrative example, the inconsistencies comprise at least one of compaction inconsistencies or a wrinkle.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram. For example, process 1100 may further comprise analyzing the plurality of comparisons to determine if at least one of an undesirable compaction or a number of wrinkles is present in the composite structure.

Figure 13:
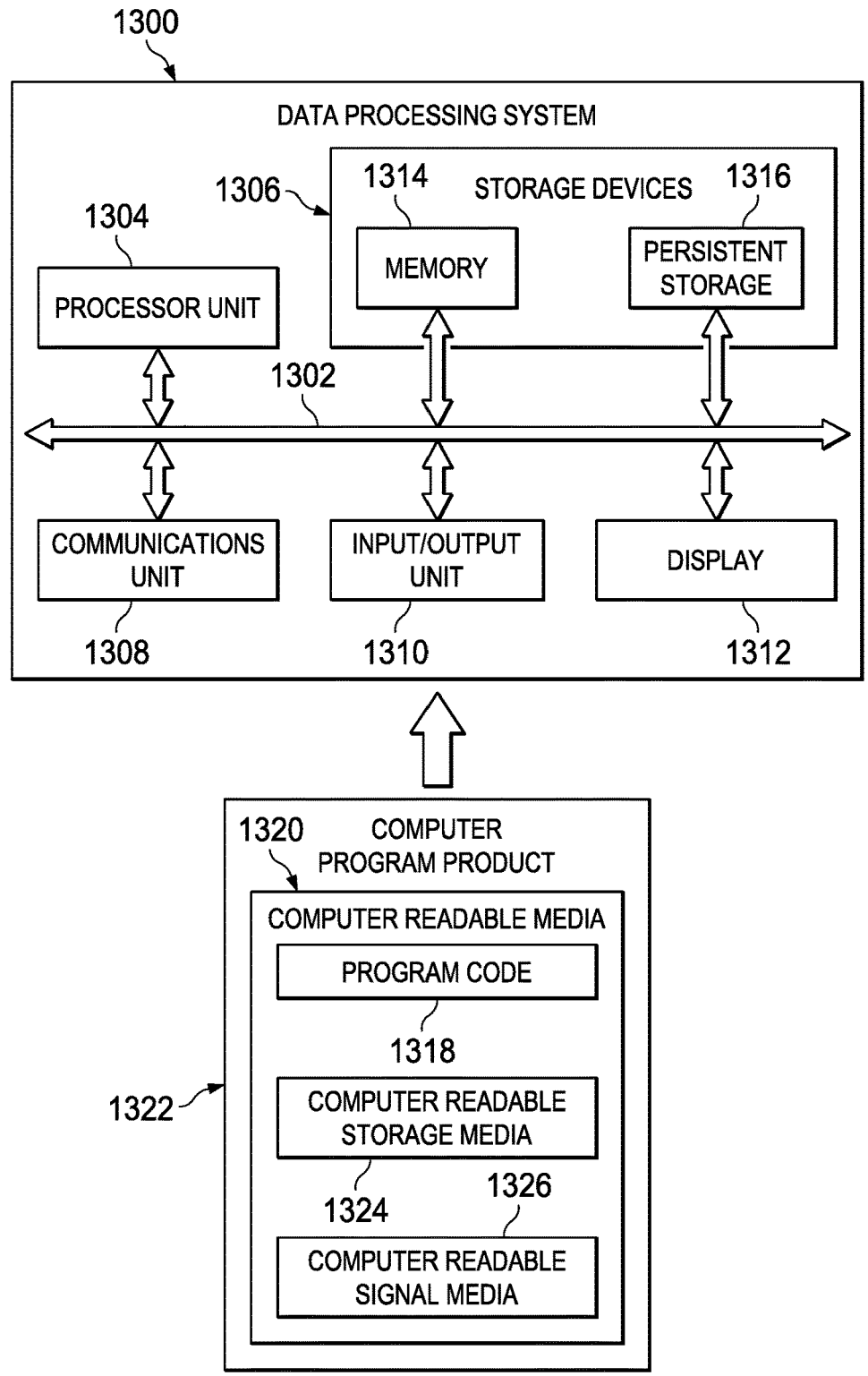
FIG. 13 is an illustration of a data processing system in the form of a block diagram in accordance with an illustrative embodiment.

Turning now to FIG. 13, an illustration of a data processing system in the form of a block diagram is depicted in accordance with an illustrative embodiment. Data processing system 1300 may be used to implement computer system 214 of FIG. 2. Data processing system 1300 may be used to process data as described in FIG. 3 and display output as depicted in FIGS. 4-8. As depicted, data processing system 1300 includes communications framework 1302, which provides communications between processor unit 1304, storage devices 1306, communications unit 1308, input/output unit 1310, and display 1312. In some cases, communications framework 1302 may be implemented as a bus system.

Processor unit 1304 is configured to execute instructions for software to perform a number of operations. Processor unit 1304 may comprise a number of processors, a multi-processor core, and/or some other type of processor, depending on the implementation. In some cases, processor unit 1304 may take the form of a hardware unit, such as a circuit system, an application specific integrated circuit (ASIC), a programmable logic device, or some other suitable type of hardware unit.

Instructions for the operating system, applications, and/or programs run by processor unit 1304 may be located in storage devices 1306. Storage devices 1306 may be in communication with processor unit 1304 through communications framework 1302. As used herein, a storage device, also referred to as a computer readable storage device, is any piece of hardware capable of storing information on a temporary and/or permanent basis. This information may include, but is not limited to, data, program code, and/or other information.

Memory 1314 and persistent storage 1316 are examples of storage devices 1306. Memory 1314 may take the form of, for example, a random access memory or some type of volatile or non-volatile storage device. Persistent storage 1316 may comprise any number of components or devices. For example, persistent storage 1316 may comprise a hard drive, a flash memory, a rewritable optical disk, a rewritable magnetic tape, or some combination of the above. The media used by persistent storage 1316 may or may not be removable.

Communications unit 1308 allows data processing system 1300 to communicate with other data processing systems and/or devices. Communications unit 1308 may provide communications using physical and/or wireless communications links.

Input/output unit 1310 allows input to be received from and output to be sent to other devices connected to data processing system 1300. For example, input/output unit 1310 may allow user input to be received through a keyboard, a mouse, and/or some other type of input device. As another example, input/output unit 1310 may allow output to be sent to a printer connected to data processing system 1300.

Display 1312 is configured to display information to a user. Display 1312 may comprise, for example, without limitation, a monitor, a touch screen, a laser display, a holographic display, a virtual display device, and/or some other type of display device.

In this illustrative example, the processes of the different illustrative embodiments may be performed by processor unit 1304 using computer-implemented instructions. These instructions may be referred to as program code, computer usable program code, or computer readable program code, and may be read and executed by one or more processors in processor unit 1304.

In these examples, program code 1318 is located in a functional form on computer readable media 1320, which is selectively removable, and may be loaded onto or transferred to data processing system 1300 for execution by processor unit 1304. Program code 1318 and computer readable media 1320 together form computer program product 1322. In this illustrative example, computer readable media 1320 may be computer readable storage media 1324 or computer readable signal media 1326.

Computer readable storage media 1324 is a physical or tangible storage device used to store program code 1318 rather than a medium that propagates or transmits program code 1318. Computer readable storage media 1324 may be, for example, without limitation, an optical or magnetic disk or a persistent storage device that is connected to data processing system 1300.

Alternatively, program code 1318 may be transferred to data processing system 1300 using computer readable signal media 1326. Computer readable signal media 1326 may be, for example, a propagated data signal containing program code 1318. This data signal may be an electromagnetic signal, an optical signal, and/or some other type of signal that can be transmitted over physical and/or wireless communications links.

The illustration of data processing system 1300 in FIG. 13 is not meant to provide architectural limitations to the manner in which the illustrative embodiments may be implemented. The different illustrative embodiments may be implemented in a data processing system that includes components in addition to or in place of those illustrated for data processing system 1300. Further, components shown in FIG. 13 may be varied from the illustrative examples shown.

Figure 14:
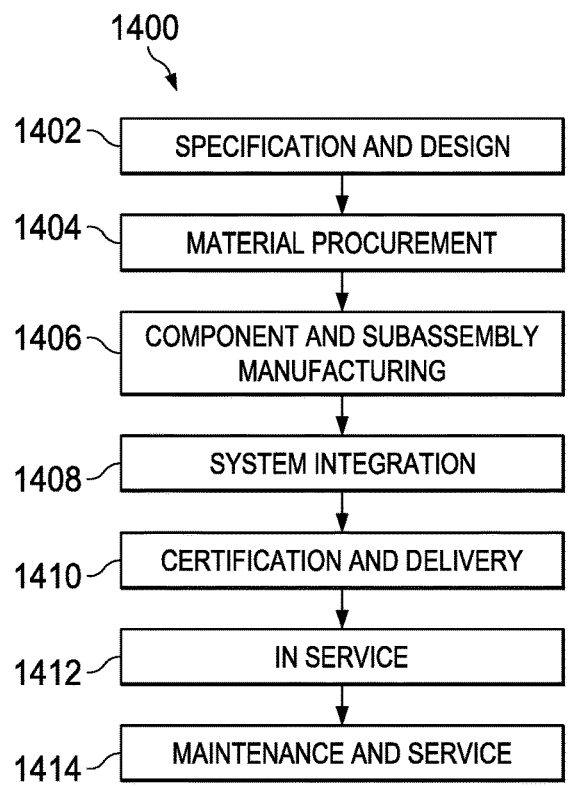
FIG. 14 is an illustration of an aircraft manufacturing and service method in the form of a block diagram in accordance with an illustrative embodiment.
Figure 15:
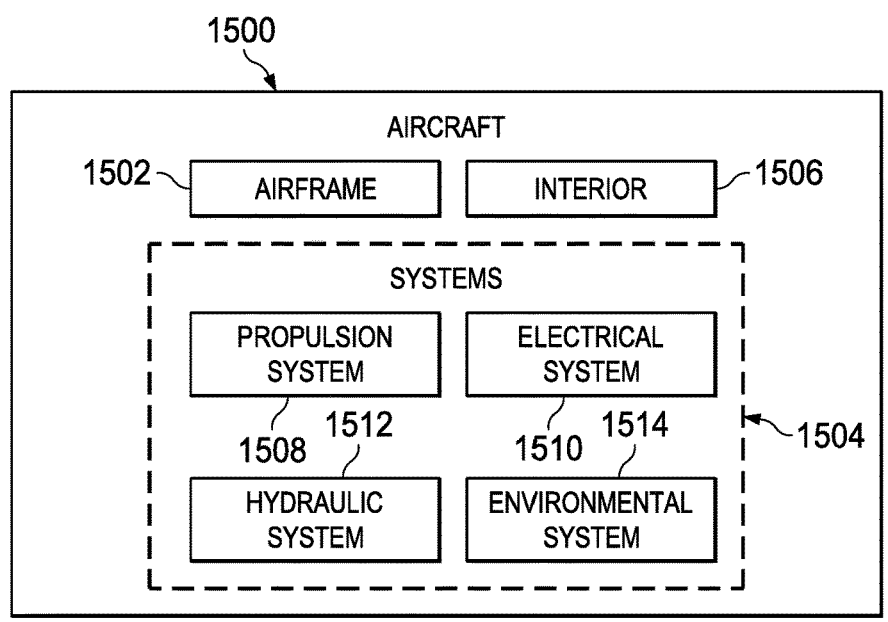
FIG. 15 is an illustration of an aircraft in the form of a block diagram in which an illustrative embodiment may be implemented.

Illustrative embodiments of the disclosure may be described in the context of aircraft manufacturing and service method 1400, as shown in FIG. 14, and aircraft 1500, as shown in FIG. 15. Turning first to FIG. 14, an illustration of an aircraft manufacturing and service method is depicted in accordance with an illustrative embodiment. During pre-production, aircraft manufacturing and service method 1400 may include specification and design 1402 of aircraft 1500 and material procurement 1404.

During production, component and subassembly manufacturing 1406 and system integration 1408 of aircraft 1500 takes place. Thereafter, aircraft 1500 may go through certification and delivery 1410 in order to be placed in service 1412. While in service 1412 by a customer, aircraft 1500 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of an aircraft is depicted in which an illustrative embodiment may be implemented. In this example, aircraft 1500 is produced by aircraft manufacturing and service method 1400 in FIG. 14, and may include airframe 1502 with plurality of systems 1504 and interior 1506. Examples of plurality of systems 1504 include one or more of propulsion system 1508, electrical system 1510, hydraulic system 1512, and environmental system 1514. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1400 in FIG. 14. One or more illustrative embodiments may be used during component and subassembly manufacturing 1406 in FIG. 14. For example, laser ultrasound inspection system 205 in FIG. 2 may be used to inspect composite structures during component and subassembly manufacturing 1406. Further, laser ultrasound inspection system 205 in FIG. 2 may be used to inspect an assembly during maintenance and service 1414 in FIG. 14. For example, composite structures of aircraft 1500 may be inspected during scheduled maintenance for aircraft 1500 using laser ultrasound inspection system 205.

Thus, one or more illustrative embodiments provide a method and apparatus for determining whether inconsistencies are present in a composite structure. A structure signal is identified. After identifying the structure signal, the structure signal is compared to a structure signal for a composite structure standard. If at least one of the frequency or the width of the structure signal is different from the structure signal of the composite structure standard, inconsistencies are present. For example, a wrinkle causes the width of the structure signal to be greater than a width of the structure signal of the composite structure standard. Further, compaction inconsistencies change the frequency of the structure signal.

By determining a structure signal, the illustrative embodiments detect inconsistencies that conventional processing would not detect. For example, the illustrative embodiments detect wrinkles or compaction inconsistencies. As another example, the illustrative embodiments determine the shape of wrinkles. Yet further, at least one of compaction or wrinkles is found and measured repeatably and confidently.

Shift in the structure signal, or 'Structural Peak,' in the frequency domain is an accurate measurement of the change in ply spacing due to compaction. Compaction measurements can be used to develop and verify composite manufacturing parameters such as temperature profiles, pressures, or tooling design. By developing and verifying composite manufacturing parameters, faster and better methodologies may be developed.

Wrinkle measurement is another application for frequency analysis using laser ultrasound inspection equipment. Wrinkle measurement may include measurement of ply compaction and rarefaction using structural peak changes in regions around the wrinkle, and mapping back to ply shape.

Shift in 'Structural Peak' of frequency space is an accurate measurement of the change in ply spacing due to compaction. The change in ply thickness over the depth of the wrinkle causes a broadening of the structural peak, and can be used to find wrinkles during scanning.

Compaction and rarefaction around wrinkles can be measured by the movement of the structural peak relative to the frequency, and used to better quantify wrinkle morphology. It can be used to improve wrinkle shape and ply orientation measurement, for better prediction of part performance and less overly-conservative (and costly) repairs.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting inconsistencies in a composite structure, the method comprising:
   directing a pulsed laser beam towards the composite structure comprised of a number of composite materials, wherein wide-band ultrasonic signals are formed in the composite structure when radiation of the pulsed laser beam is absorbed by a surface of the composite structure;
   detecting the wide-band ultrasonic signals over a duration of time to form data, wherein the data comprises an ultrasonic A-scan spectrum;
   processing the data to identify a structure signal in a frequency domain of the ultrasonic A-scan spectrum, wherein processing the data comprises:
      applying a moving time-window in a time domain to an ultrasonic A-scan to form time-windowed signals, wherein the moving time-window has a Gaussian shape sized to contain between two and five plies of the number of composite materials; and
      determining at least one of a mean frequency or a maximum frequency of a Fourier spectrum taken for each of the time-windowed signals, including determining a maximum frequency of a windowed signal of an ultrasonic A-scan using the equation $S_n = \Sigma_{k=1}^{P} \alpha_k * S_{n-k}$, where $S_n$ is an A-scan signal at sample point n, p is a quantity of coefficients, $\alpha_k$ is a $k^{th}$ Fourier coefficient, and $S_{n-k}$ is the A-scan signal at prior sample point n-k; and
   determining whether the inconsistencies are present in the number of composite materials by comparing the structure signal of the ultrasonic A-scan spectrum to a structure signal of a composite structure standard.

2. The method of claim 1, wherein determining whether the inconsistencies are present in the number of composite materials comprises:
   determining whether a first width of the structure signal of the ultrasonic A-scan spectrum in the frequency domain differs from a second width of the structure signal of the composite structure standard in the frequency domain.

3. The method of claim 2, wherein determining whether the inconsistencies are present in the number of composite materials further comprises:
   determining a wrinkle is present in the number of composite materials if the first width differs from the second width.

4. The method of claim 1, wherein determining whether the inconsistencies are present in the number of composite materials comprises:
   determining whether the structure signal of the ultrasonic A-scan spectrum is shifted in the frequency domain relative to the structure signal of the composite structure standard.

5. The method of claim 4, wherein determining whether the inconsistencies are present in the number of composite materials further comprises:
   determining compaction of the number of composite materials is undesirable if the structure signal of the ultrasonic A-scan spectrum is shifted in the frequency domain relative to the structure signal of the composite structure standard.

6. The method of claim 1, wherein the wide-band ultrasonic signals are detected using a point detector.

7. A method comprising:
   directing a pulsed laser beam towards a composite structure comprised of a plurality of layers, wherein wide-band ultrasonic signals are formed in the composite structure when radiation from the pulsed laser beam is absorbed by a surface of the composite structure;
   detecting the wide-band ultrasonic signals over a duration of time to form data, wherein the data comprises a plurality of ultrasonic A-scans for at least a portion of the composite structure;
   applying a moving time-window in a time domain to each of the plurality of ultrasonic A-scans, wherein the moving time-window has a Gaussian shape sized to contain between two and five plies of the number of composite materials;
   determining a frequency measurement within the moving time-window for each of the plurality of ultrasonic A-scans, including determining a maximum frequency of a windowed signal of an ultrasonic A-scan using the equation $S_n = \Sigma_{k=1}^{P} \alpha_k * S_{n-k}$, where $S_n$ is an A-scan signal at sample point n, p is a quantity of coefficients, $\alpha_k$ is a $k^{th}$ Fourier coefficient, and $S_{n-k}$ is the A-scan signal at prior sample point n-k;
   determining a structure signal in a frequency domain of an ultrasonic A-scan spectrum for each of the plurality of ultrasonic A-scans using the frequency measurement; and
   comparing the structure signal of each ultrasonic A-scan spectrum of the plurality of ultrasonic A-scans to a structure signal for a composite structure standard to form a plurality of comparisons.

8. The method of claim 7, wherein the frequency measurement is selected from a mean frequency or a maximum frequency.

9. The method of claim 7 further comprising: analyzing the plurality of comparisons to determine if at least one of an undesirable compaction or a number of wrinkles is present in the composite structure.

10. The method of claim 7, wherein comparing the structure signal of each ultrasonic A-scan spectrum of the plurality of ultrasonic A-scans to the structure signal of the composite structure standard comprises: comparing a respective width of each structure signal of each respective ultrasonic A-scan spectrum of the plurality of ultrasonic A-scans to a width of the structure signal of the composite structure standard.

11. The method of claim 7, wherein comparing the structure signal of each ultrasonic A-scan spectrum of the plurality of ultrasonic A-scans to the structure signal of the composite structure standard comprises: comparing a respective location of each structure signal of each respective ultrasonic A-scan spectrum of the plurality of ultrasonic A-scans in the frequency domain to a location of the structure signal of the composite structure standard in the frequency domain.

* * * * *